(12) United States Patent
Song et al.

(10) Patent No.: US 8,600,149 B2
(45) Date of Patent: Dec. 3, 2013

(54) METHOD AND SYSTEM FOR ELECTRONIC INSPECTION OF BAGGAGE AND CARGO

(75) Inventors: Samuel Moon-Ho Song, Las Vegas, NV (US); Douglas Perry Boyd, Las Vegas, NV (US)

(73) Assignee: TeleSecurity Sciences, Inc., Las Vegas, NV (US)

(*) Notice: Subject to any disclaimer, the term of this patent is extended or adjusted under 35 U.S.C. 154(b) by 1224 days.

(21) Appl. No.: 12/197,687

(22) Filed: Aug. 25, 2008

(65) Prior Publication Data
US 2010/0046704 A1    Feb. 25, 2010

(51) Int. Cl.
*G06K 9/00* (2006.01)

(52) U.S. Cl.
USPC ............................................. 382/143; 378/57

(58) Field of Classification Search
USPC ................ 382/141, 143; 209/509; 414/788.7; 378/57
See application file for complete search history.

(56) References Cited

U.S. PATENT DOCUMENTS

| | | | |
|---|---|---|---|
| 5,974,111 A * | 10/1999 | Krug et al. | 378/57 |
| 6,088,423 A * | 7/2000 | Krug et al. | 378/57 |
| 6,735,593 B1 * | 5/2004 | Williams | 1/1 |
| 7,260,173 B2 * | 8/2007 | Wakayama et al. | 378/19 |
| 2004/0022356 A1 * | 2/2004 | Subotic et al. | 378/57 |
| 2004/0062346 A1 * | 4/2004 | Fernandez | 378/41 |
| 2004/0167716 A1 * | 8/2004 | Goncalves et al. | 701/217 |
| 2005/0276443 A1 * | 12/2005 | Slamani et al. | 382/103 |
| 2006/0056586 A1 * | 3/2006 | Uetake et al. | 378/57 |
| 2006/0104414 A1 * | 5/2006 | Mayo | 378/57 |
| 2006/0273257 A1 * | 12/2006 | Roos et al. | 250/358.1 |
| 2007/0168467 A1 * | 7/2007 | Hu et al. | 709/219 |
| 2008/0062262 A1 * | 3/2008 | Perron et al. | 348/82 |
| 2008/0152082 A1 * | 6/2008 | Bouchard et al. | 378/57 |
| 2008/0170660 A1 * | 7/2008 | Gudmundson et al. | 378/57 |
| 2009/0034790 A1 | 2/2009 | Song et al. | |
| 2010/0076959 A1 * | 3/2010 | Ramani et al. | 707/722 |

OTHER PUBLICATIONS

T. Funkhouser, et al.; "A Search Engine for 3D Models"; ACM Transactions on Graphics, vol. 22, No. 1, pp. 83-105, 2003.

Morris etal;"Real Spherical Harmonic Expansion Coefficeints as 3D Shape Descriptors for Protein Binding Pocket & Ligand Comparisons";Bioinformatics,vol. 21,No. 10,p. 2347-2355,2005.

M. Kazhdan et al.;"Rotation Invarient Spherical Harmonic Representation of 3D Shape Descriptors"; Eurographics Symposium on Geometry Processing 2003; 9 pgs.

W. Lorensen et al.;"Marching Cubes: A High Resolution 3D Surface Construction Algorithm"; Computer Graphics, vol. 21, No. 4, Jul. 1987.

A. Bonnel et al.; 'Quantitative Air-Trapping Analysis in children with Mild Cystic Fibrosis Lung Disease; Pediatric Pulmonology, vol. 38, pp. 396-405, 2004.

(Continued)

*Primary Examiner* — Shervin Nakhjavan
(74) *Attorney, Agent, or Firm* — The Small Patent Law Group; Dean D. Small

(57) ABSTRACT

A method and system of electronically inspecting baggage comprises generating scan data representative of a piece of baggage. At least one of a contour and a surface is extracted from the scan data, and the at least one of a contour and a surface is representative of an object within the baggage. An object database comprises data representative of shapes of known objects, and the at least one of a contour and surface is compared to the object database to identify an object match which is presented.

22 Claims, 6 Drawing Sheets

(56) References Cited

OTHER PUBLICATIONS

Paolo Sabella; "A Rendering Algorithm for Visualizing 3D Scalar Fields", ACM 0-89791-275-6/88/008/0051, 1988, pp. 51-58.

Chin-Feng Lin, Don-Lin Yang, and Yeh-Ching Chung; "A Marching Voxels of Method for Surface Rendering of Volume Data", Department of Information Engineering, IEEE, 2001, pp. 306-313.

Kelly Leone and R. Liu, "Validating Throughput analysis of Checked Baggage Screening Performance", Jul. 2004, pp. 1-17.

Jayaram K. Udupa and Hsui-Mei Hung, "Surface Versus Volume Rendering: A comparative Assessment", IEEE, 1990, pp. 83-91.

Yi Sun, "Performance Analysis of Maximum Intensity Projection Algorithm for Display of MRA Images", IEEE, vol. 18, No. 12, Dec. 1999, pp. 1154-1169.

Sameer Singh and Maneesha Singh, Explosives detection systems (EDS) for aviation security, Signal Processing 83, pp. 31-55, Jun. 2002.

Sally L. Wood, "Visualization and Modeling of 3-D Structures", IEEE Engineering in Medicine and Biology, Jun. 1992, pp. 72-79.

Ulf Tiede, Karl Heinz Hoehne, Michael Bomans, Andreas Pummert, Martin Riemer, and Gunnar Wiebecke; "Surface Rendering: Investigation of Medical 3D-Rendering Algorithms", Mar. 1990.

Marc Levoy; "Volume Rendering: Display of Surfaces from Volume Data", IEEE May 1988, pp. 29-37.

Steven Schreiner; "A Fast Maximum-Intensity Projection Algorithm for Generating Magnetic Resonance Angiograms", IEEE 1993, 0278-0063/93, pp. 50-57.

R.C. Gonzalez and R.E. Woods; "Image Segmentation"; Digital Image Processing; Second Edition; Prentice Hall, New Jersey, 2002; Chapter 10, pp. 567-624.

\* cited by examiner

METHOD AND SYSTEM FOR ELECTRONIC INSPECTION OF BAGGAGE AND CARGO

BACKGROUND OF THE INVENTION

Certain embodiments generally relate to methods and systems for electronically evaluating baggage scanned images.

In recent years there has been increasing interest in the use of imaging devices at airports to improve security. Today, thousands of computed tomography (CT) scanners are installed at airports to scan checked baggage. The CT scanners generate data sets that are used to form images representative of each scanned baggage. The data sets are currently processed by an automated image recognition system, such as for certain patterns, characteristics and the like. When the image recognition system identifies a potential threat, the images are brought to the attention of a local operator, for example, who is located at an airport.

The CT scanners, also referred to as explosive detection systems (EDS), are capable of producing full 3-dimensional (3-D) images. However, the software required to view such 3-D images is complex and generally requires sophisticated local operators with expertise in 3-D rendering software tools. CT scanners are able to generate a 3-D voxel data set that represents the volume of the scanned bag. Conventional CT scanners provide 3-D images by stacking a series of closely spaced cross section images into a 3-D matrix. The 3-D images may then be viewed by a local operator/screener. The local operator at the airport terminal usually steps through two-dimensional (2-D) CT slices (e.g., planes) of the 3-D matrix to detect and identify potential threats within the packed bag.

Currently, existing CT based EDS are deployed at airports to detect various threats within packed bags. The suspicious baggages are passed on to a human screener who examines individual 2D CT slice images of the scanned baggage. The CT slice images of alarmed bags are carefully examined by the human screener who then either accepts or redirects the baggage for explosive trace detection (ETD) and/or manual unpacking for a visual inspection.

After the baggage is checked-in, the baggage is scanned by a CT scanner and axial slices or images are created of the baggage. The local operator/screener views the axial slices or images by scrolling through each image slice one by one to determine if any potential threats are present in an image. Scrolling through over dozens of images (or even more for future generation scanners) for each bag is a laborious task, and the local operator/screener must be alert to detect features of any potential threats within an image in order to flag the possible threats. Examination of each axial slice image gives rise to operator/screener fatigue that eventually will lead to sub-optimal performance by the operator causing him/her to miss some threats. The CT 3-D data set of a packed baggage may include hundreds of axial slice images. Of these images only a few images may show the potential threat. If the local operator misses any one of these few images, the undetected threats could result in disaster either while a plane, train, ship, or cargo vessel is in transit or upon arrival at the destination.

There is a need for an improved baggage scanning system and method to allow baggage and cargo to be quickly screened while improving performance in detection of undesired objects, such as contraband, weapons and explosives, both in automated detection systems and systems operated partially or completely by an operator.

BRIEF DESCRIPTION OF THE INVENTION

In accordance with certain embodiments, a method is provided for electronically inspecting baggage that comprises generating scan data representative of a piece of baggage. Contour and/or surface information is extracted from the scan data, wherein the contour and/or surface information is representative of an object within the baggage. An object database is provided that comprises shape information, such as 3D object descriptors or shape functions, representative of shapes of known objects. The extracted contour or surface information from the scan data is compared to that of the database to determine when an object match is present. Optionally, before the comparison, the method may include computing modeling coefficients, such as spherical harmonic coefficients, based on the extracted contour and/or surface information. The modeling coefficients are then compared to modeling coefficients for shape functions or 3D object descriptors stored in the object database.

According to at least one embodiment, a system for electronically inspecting baggage is provided that comprises a database to store scan data acquired while scanning a piece of baggage. The system has an object database that stores shape information, such as shape functions or 3D object descriptors corresponding to known objects. A workstation compares the scan data to the shape functions to determine if an object match is detected and a display displays information related to the object match.

In accordance with yet another embodiment, a computer readable medium is provided that stores an application for use to inspect baggage where scan data has been generated that is representative of a piece of baggage. The scan data is stored at a first memory and the application comprises instructions configured to direct a computer to obtain the scan data from the first memory. The instructions direct the computer to extract at least one of contour and surface information from the scan data. The at least one of contour and surface information are representative of an object within the baggage. The instructions direct the computer to compare the at least one of contour and surface information to shape information in an object database to identify an object match and present the object match on a display.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which is shown by way of illustration specific embodiments in which the present invention may be practiced. It is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. Also as used herein, the phrase "an image" is not intended to exclude embodiments of the present invention in which data representing an image is generated, but a viewable image is not generated. Therefore, as used herein, the term "image" broadly refers to both viewable images and data representing a viewable image. However, many embodiments generate (or are configured to generate) at least one viewable image. The terms "bag", "cargo" and "baggage" as used throughout shall refer broadly to a bag, bottle, box, container, cargo, clothing, luggage, suitcase, carry-on item, personnel belongings, and the like.

An inspection system is provided to allow for electronic inspection of passenger baggage or cargo shipment and to detect 3-D objects there-within. Baggage is scanned to obtain 2-D or 3-D data sets from which 2-D and 3-D images, respectively, may be generated. For example, 2-D line scanners (e.g. Threat Image Projection Ready X-ray or TRX) and 3-D CT scanners (e.g. Explosive Detection System or EDS) for baggage as well as scanners based on other sources of high energy may be used. From the data sets, contour information of structures within the 2-D images and/or surface information of structures within the 3-D images are extracted. The extraction of at least one of contour and surface information may be performed with a partially available data set or a truncated data set that only represents a portion of the object. An object database of 3-D objects is accessed to determine if the contour or surface is a match to a known object. The database includes many known objects which may be classified as benign or as dangerous, such as a knife, gun or potential explosive. Detected objects may be reported for further review and/or inspection.

Figure 1:
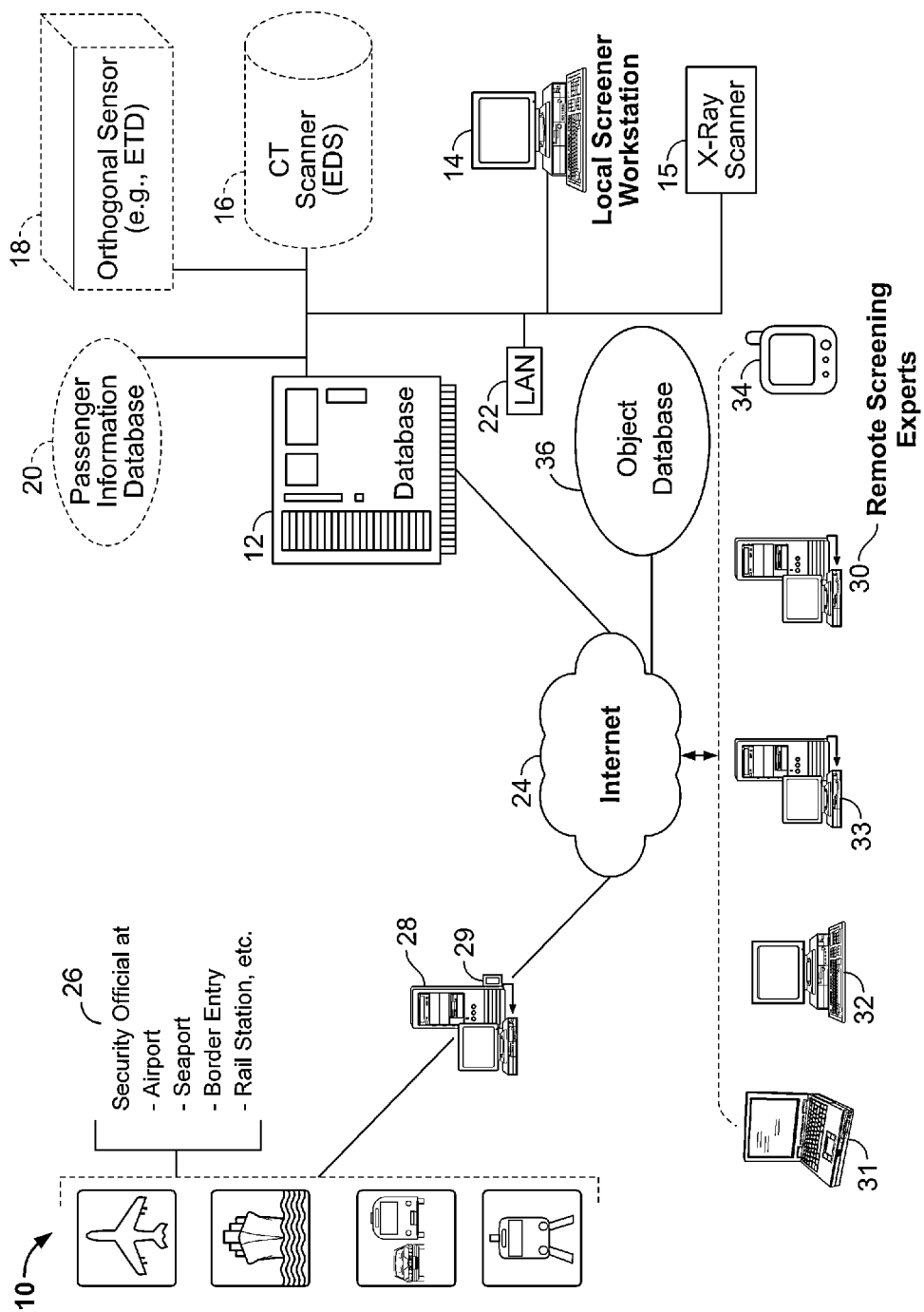
FIG. 1 illustrates a block diagram of an inspection system for baggage and cargo formed in accordance with an embodiment of the invention.

FIG. 1 illustrates a block diagram of an inspection system 10 for baggage and cargo formed in accordance with an embodiment of the invention. The system 10 may be used by various security officials to evaluate baggage. By way of example only, the security official may represent a transportation screening officer, customs officials, a transportation security officer (TSO), homeland security officers, airport employees, building (government and private) security agents, police, guards, contraband inspectors and the like. The system 10 may include one or more of a database 12, a workstation 14, an x-ray scanner 15, a CT scanner 16, an orthogonal sensor 18, and a passenger information database 20 that are communicatively interconnected together by a local area network 22 (e.g., LAN). When a passenger enters, for example, a terminal to board an airplane, a boat, a bus, a train, and the like, the passenger's checked and carry-on baggage are scanned during a check-in process. During the check-in process different characteristics of objects contained within the baggage are examined to determine the presence of any object of interest (e.g., explosives, guns, knifes, contraband, agricultural produce, money, drugs, and the like). For example, other sensors 18 may also be included to provide different (or orthogonal) characteristics of the baggage. The sensors 18 may measure gases, particles, electro magnetic fields, ultrasound, x-rays, CT, infrared, heat characteristics and the like. The CT scanner 16 may include a moving source and moving detector. The x-ray scanner 15 may include a stationary source and stationary detector that operate as a line scanner. The x-ray and CT scanners 15 and 16 generate scan data representative of the scanned baggage. The CT scanner 16 may be used to scan checked baggage and/or carry-on baggage. Similarly, the x-ray scanner 15 may be used to scan checked baggage and/or carry-on baggage. The scan data may represent a projection view from a fixed, known scan angle (such as with a stationary source and detector). Optionally, the scan data may represent a series of projection views from multiple scan angles about a z-axis (such as with multiple fixed sources and detectors or one or more rotating source and detector). When the scan data comprises a series of projection views, the scan data may be used to reconstruct a volumetric data set, from which rendered views may be produced.

The acquired raw scan data, volumetric or 2-D data sets and/or rendered views are stored in the database 12 via a high-speed connection, such as the LAN 22. When the scan data corresponds to one projection view, the projection view may also be stored in the database 12. Passenger information from the passenger information database 20 maybe linked or indexed to the stored scan data to associate a particular passenger with the scan data of the passenger's baggage. Various passenger information data, such as passenger itinerary, travel history, credit information, passenger profile, passport information, passenger photograph, family history, age, physical characteristics, job information and the like may be stored in the database 12 and/or obtained from a remote location and then made available for review to assist in deciding whether the results of the detected object comparison process indicates a possible threat.

The database 12 is connected to a network 24. The network 22 and/or network 24 may represent the Internet, a private network, a high-speed network, an intranet, the world wide web, a local area network (LAN), a wide area network (WAN), a peer-to-peer network, a client/server network, metropolitan area network (MAN) and the like to provide access to the database 12.

An object database 36 is connected to the network 24 and may be connected to the network 22. The object database 36 stores shape information corresponding to known objects, providing a library of templates, pre-existing models, surfaces, contours and the like for numerous identified objects. The shape information may be stored as parameters defining an enclosed 3D surface or 2D contour. Shape information may be included in the object database 36 for objects that are potentially dangerous and/or illegal to transport, such as guns, knives, explosives, contraband, money, drugs, fruits, vegetables and the like. Also, shape information for an object may be included in the object database 36 because the object is benign and it is desired to electronically and automatically identify and dismiss the object. Therefore, typical items that may be found in luggage may also be included in the object database 36.

The object database 36 may be a commercially available object database, such as those used in animation and computer and web graphical programs. The object database 36 may include data from more than one commercial object database. Alternatively or in addition to, the object database 36 may be built of scanned CT images. Furthermore, additional objects may be added to the database as desired.

The object database 36 may further store rotation insensitive surface and/or contour data representative of each of the objects. The rotation insensitive data may be generated based on spherical harmonics, such as spherical harmonic coefficients, attributes or parameters. The rotation insensitive data may be indexed to allow quicker matching to occur.

A security official 26 may be located at a variety of locations, for example, at an airport, a seaport, a border entry post, a rail station, a government building, a public building, a courthouse and the like. The security official 26 accesses the database 12 via a workstation 28 and the network 24 to inspect the baggage. For example, the security official 26 may review the data prior to the baggage and cargo being loaded, or may review the data when the baggage is aboard an airplane, for confiscation or other further action upon arrival at the destination port. There may be multiple workstations 28, for use by customs officials 26, located in multiple terminals, sites, countries or geographic areas. The workstations 28 have network interfaces 29 to simultaneously access the database 12 and the object database 36 via the network 24. The workstations 28 review results of the comparison of scan data from the database 12 and the object database 36. For example, a security official 26 may review the scan data from the database 12 and corresponding potential images or other data from the object database 36 that may indicate that the baggage holds a potential threatening or disallowed object. The object database 36 may provide one or more of text descriptions, graphics, images, recommendations and the like with respect to the potential threatening or disallowed object.

For one piece of baggage, hundreds of slices or images may be generated, a subset or all of which are compared to data within the object database 36. Other image processing may also be accomplished in parallel with the contour and surface information comparison. Additional data may be used to identify whether various objects within the baggage are innocuous or not, such as based on the Hounsfield unit value. For example, two objects may have very similar contours. Hounsfield unit values or attenuation data may be used to help determine which object is a better match. Also, electronic unpacking may be used to determine a substantially close approximation of the volume for each object, both threats and innocuous objects, as well as contraband objects, within the packed baggage.

A security official 26 may contact remote screening experts 30 for assistance in determining if an object is a threat. The security official 26 and one or more remote experts 30 with access to the network 24 are able to examine the views of the object from the baggage, such as projection and rendered views, together with the potential matches of one or more objects from the object database 36 and discuss whether an object is a threat or not a threat. The remote screening experts 30 may utilize a variety of modes to view the data, for example, a laptop 31, a desktop 32, a workstation 33, a personal digital assistant/cell phone 34, and the like.

Figure 2:
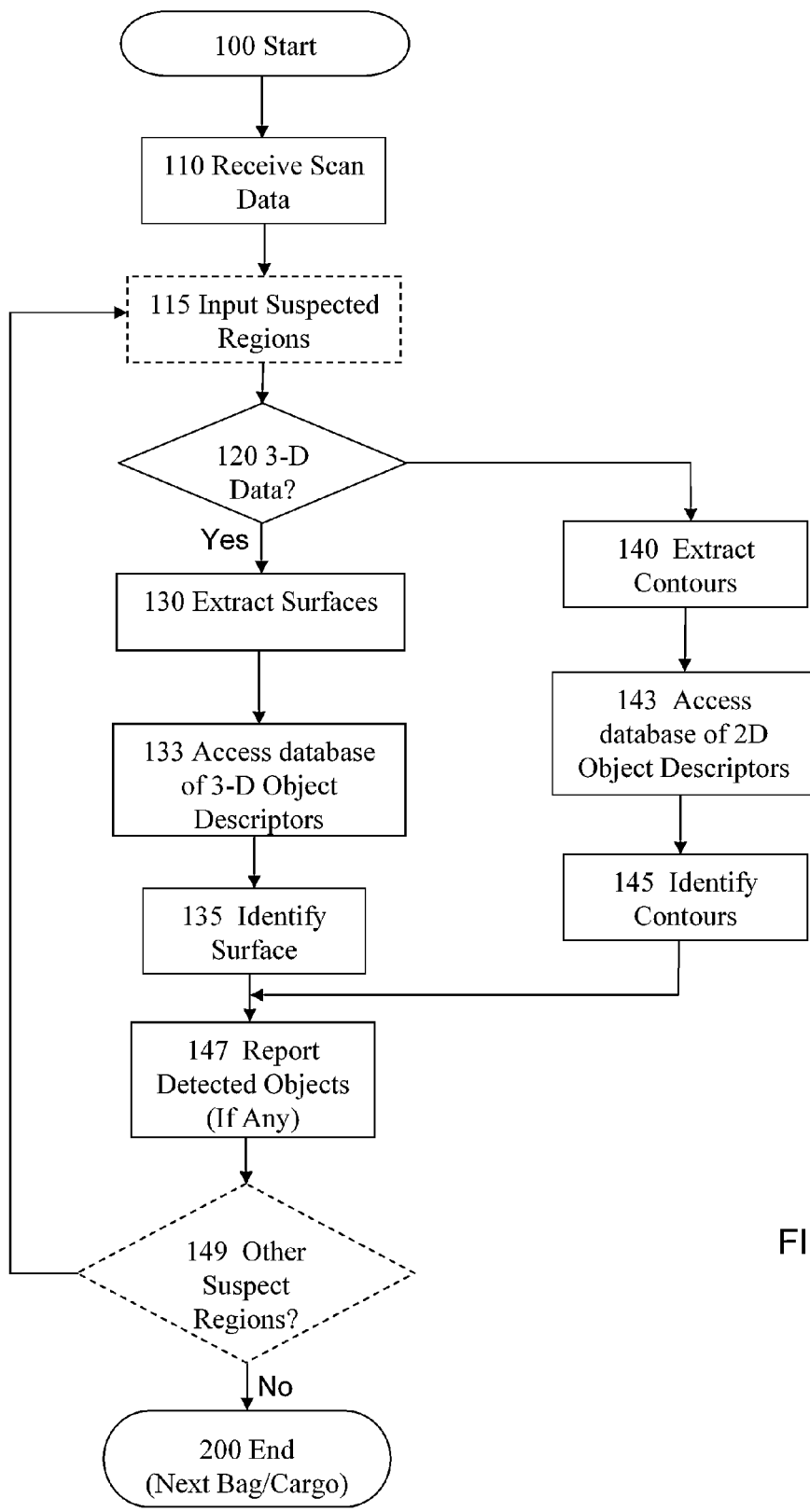
FIG. 2 illustrates a method for comparing scan data to the object database in order to identify objects of interest within baggage performed in accordance with an embodiment of the invention.

FIG. 2 illustrates a method for electronically inspecting baggage in accordance with an embodiment by comparing scan data to the object database 36 in order to identify objects of interest within baggage such as contraband, weapons, explosives, agricultural products and/or other undesirable objects. As discussed previously, the object database 36 comprises shape information used to describe the surface shape of objects, for example, a gun, knife, detonator, batteries, money, drugs, agricultural products, and the like. Also, shape information for other objects may be stored, including benign objects that may generate false alarms of existing EDS systems. It should be understood that the method of FIG. 2 may be implemented together with existing scanning and detection processes, or may be implemented as a stand-alone detection process.

At 100, a scanning device or scanner 16 (e.g., such as a CT scanner, a cine computed tomography scanner, a helical CT scanner, a four-dimensional (4D) cine computed tomography scanner, an electronic beam scanner, an X-ray scanner, a dual-energy x-ray scanner, dual-energy CT scanner, and the like) scans the baggage (e.g., luggage, suitcases, backpacks, boxes, crates, briefcases, and the like) or cargo. In one embodiment, a volumetric data set representative of every voxel within the baggage may be obtained. In another embodiment, multiple slices or views may be obtained. Optionally, the multiple slices or views may intersect each other such that a surface of an object may be interpolated based on the multiple slices or views. The scanner 16 may scan for a scannable characteristic to acquire scan data representative of a content of the piece of baggage, wherein the scannable characteristic is an attenuation measure. Each scanner 16 includes a scanner source and detector that are capable of obtaining a volumetric, cross-sectional, or intersecting cross-sectional scans of each item of interest, a controller module to control operation of the scanner 16, a user interface to afford operator control, and a monitor to display images obtained by the scanner 16. For example, the scanner and detector may rotate about the baggage as the baggage is conveyed along a belt (e.g., to perform a helical scan).

At 110 the scan data is obtained and stored in the database 12 and various processing, such as segmentation, may be accomplished. The scan data provides axial slices (or z-slices) with isotropic pixels, and shape data may be determined based on, for example, density and connectivity. The following example is directed to 3-D image data set, but similar processing may be applied to 2-D image data sets. A volumetric data set is generated from the scan data, where the volumetric data set includes voxel values that are in Hounsfield units. A portion of the volumetric data set is segmented based on the voxel values to identify an object and provide a visual marker outlining the object. The data set may be initially segmented by determining the edges and borders of one or more objects within the volumetric data set by connecting together voxels having similar or common Hounsfield unit values. For example, groups or clusters of voxels may be connected together using a 3-D connectivity algorithm, such as a marching-cubes algorithm, a marching voxel algorithm, a 3-D region growing algorithm and the like. Segmentation algorithms such as gradient filters and thresholding may also be used, as well as volume growing to detect boundaries of objects. Optionally, a surface of each object may be obtained by calculating an average of each of the connected voxels and utilizing a smoothing algorithm. Alternatively, the surface of an object may be calculated based on gradient or thresholding algorithms.

Optionally, at 115, certain regions or portions of the scan data may be designated or flagged as potentially suspect. For example, the user laptops 31, desktops 32, workstations 33 and the like may be provided with a user interface feature that permits a security official to manually identify regions on 2D images or portions of a 3D volume that may contain objects of interest. The identification may be through circling areas in one or more images, clicking on an object in one or more images, and the like.

Alternatively, the suspect regions or portions may be automatically identified by an object detection algorithm. The object detection algorithm may analyze the volumetric data set, or one or more 2D or 3D images produced from the scan data. The object detection algorithm may identify objects by comparing contours or surfaces with the scan data to known contours or surfaces. When suspect regions are identified at 115 a list of suspect regions is produced. Optionally, the operation at 115 may be omitted entirely. Next, flow moves to 120.

The Hounsfield unit values may also be utilized in a threat detection algorithm that is running parallel to the object detection algorithm. Each voxel may be classified into one of several categories based on its Hounsfield unit value, such as innocuous, organic, steel, and the like. Low Hounsfield unit values may correspond to voxels for air or water and are classified as innocuous; medium Hounsfield unit values may correspond to voxels classified as organic material (e.g., shampoo or explosives); and high Hounsfield unit values may correspond to voxels classified as aluminum or steel (e.g., for guns or knives).

At 120, it is determined whether the scanner 16 generates 3-D scan data, or 2D scan data. When 3D scan data is obtained, flow moves to 130 where exterior surfaces are extracted based on the scan data. For example, the exterior surface may be identified as the outermost pixels of the segmented data within each Hounsfield unit range. Optionally, surface boundary voxels may be determined using a threshold value from the isotropic volume data. The extracted surfaces are characterized by shape information.

At 133, the object database 36 is accessed. The object database 36 stores shape information, such as a plurality of 3D object descriptions, each of which may constitute one or more shape functions. For example, the database 36 may store numerous shape functions that define shapes of known objects, such as objects representing threats, contraband, innocuous items and the like. As explained below, the shape functions may represent rotation invariant basis functions. A basis function describes the shape of the surface of an object within a coordinate system, such as the spherical coordinate system. One or more basis functions may be stored as a group to form a 3D object descriptor. At 133, multiple 3D object descriptors are accessed in the object database 36.

At 135 the extracted surface information is compared to surfaces within the object database 36. Shape matching algorithms may be used to match extracted surface information of an object within the baggage to 3D object descriptors within the object database 36. Shape matching algorithms may use scale and translation normalizations and may rotate the extracted surface information to determine if a match exists.

Returning to 120, when the scanner 16 generates 2-D scan data, flow moves to 140. At 140, contours are extracted based on the scan data. For example, the scanner 16 may be a line scanner that has more than one source, each source of which may be collimated to generate more than one image or slice. The scanner 16 may then generate 4, 6 or more images at different orientations. A contour may be extracted based on one or each of the images. The contours are characterized by contour information. Optionally, the extracted contour may be extracted based on a subset of the images. At 143, the object database 36 is accessed. The 3D object descriptors are converted to 2D object descriptors. For example, the 3D shape associated with 3D object descriptors may be projected onto different 2D views to form 2D object descriptors. Alternatively, the object database 36 may store 2D object descriptors that are directly accessed at 143. At 145 the extracted contour information is compared to the 2D object descriptors within the object database 36

At 147, detected objects are reported when an object of interest is detected to potentially represent a threat or otherwise to be of interest. At 149, it is determined whether other suspect regions were identified at 115, and if so, flow returns to 115, where the next suspect region is analyzed at operations 120 to 145. When, at 149, no more suspect regions exist within the current piece of baggage, flow moves to 200, where the next piece of baggage is examined.

At 147 results of the comparison may be displayed or otherwise reported. For example, results that indicate a potential threat or contraband may be displayed, such as displaying images associated with the surface and/or contour that was matched to a gun or knife. In another embodiment, results that further indicate items that were cleared as benign may be displayed. For example, the algorithm may detect the presence of objects that may be batteries. These results may be displayed, such as for further review and clearance by personnel, but may not generate an alarm without further information being met, such as the additional presence of detected organic material that may be explosive material.

Exemplary types of object descriptors and rotation invariant basis functions are described next. The enclosing surface of a 3D object may be represented mathematically utilizing various parameters. Certain types of parameters are dependent upon the position of the object relative to an incident viewing angle and direction and/or relative to an orientation and position of the object in a coordinate system. A slight rotation of the 3-D object can result in a different representation that can increase the time needed for recognition and identification while the match is performed for additional rotations. For object databases 36 that have many objects, it may be desirable to reduce the time needed to compare the detected contours and surfaces to data within the object database 36.

In accordance with certain embodiments, the 3-D shapes may be represented through rotation invariant basis functions such as spherical harmonics. The 3-D spherical harmonic basis functions form orthogonal solutions of Laplace's equation in spherical coordinates. The spherical harmonic functions can be used to describe the shapes of the enclosing surface of 3-D objects. The 3D object descriptors in the object database 36 may be indexed by the 3-D spherical harmonic shape descriptor, allowing faster identification.

Each 3-D object descriptor can be represented as a weighted sum of spherical harmonic basis functions where each basis function depends on azimuthal and longitudinal angles, namely $\phi$ and $\theta$, respectively. Through appropriate grouping of basis functions, e.g., by choosing the order of summation, the representation can be rotation invariant. Mathematically, the 3-D object descriptor can be represented as a weighted sum of spherical harmonic basis functions as shown in Equation 1.

$$f(\theta, \phi) = \sum_{l=0}^{\infty} \sum_{m=-l}^{l} f_{lm} Y_l^m(\theta, \phi) \quad \text{Equation 1}$$

The spherical harmonic basis functions can be expressed as:

$$Y_l^m(\theta, \phi) = \sqrt{\frac{(2l+1)(l-m)!}{4\pi(l+m)!}} P_l^{(m)}(\cos\theta)e^{im\phi} \quad \text{Equation 2}$$

where $P_l^{(m)}(\bullet)$ is the Legendre polynomial of degree l and order m. The expression for the computation of spherical harmonic coefficients can be derived by integrating both sides of Equation 1 as shown in Equation 3:

$$f_{lm} = \int_{\theta=0}^{\pi}\int_{\phi=0}^{2\pi} f(\theta,\phi)(Y_l^m(\theta,\phi))^* d\phi \sin\theta d\theta \quad \text{Equation 3}$$

where "*" denotes complex conjugate. Equation 3 may be used, for example, to compute the spherical harmonic coefficients of an object within a piece of baggage prior to comparison with the object database 36. The spherical harmonic basis functions $Y_l^m(\theta,\phi)$ form a complete set of orthonormal basis for a vector space and Equations 1 and 2 are exact in the usual $L_2$ sense. In addition, the set of spherical harmonics for the fixed frequency l form a rotation group.

$$V_l = \text{span}\{Y_l^m(\theta,\phi)\}_{m=-l}^{l} \quad \text{Equation 4}$$

As seen in Equation 4, the space $V_l$ is an irreducible representation of SO(3). It should be noted that the space $V_l$ includes all "surface frequency components" up to the fixed frequency l. Therefore, the projection operator $P_l$ onto the space $V_l$ commutes with an arbitrary rotation operator R. Equation 5 denotes the projection of a surface f onto the subspace $V_l$:

$$P_l f(\theta,\phi) = f_l(\theta,\phi) = \sum_{m=-l}^{l} f_{lm} Y_l^{(m)}(\theta,\phi) \quad \text{Equation 5}$$

Therefore, by summing all frequency components, the original function can be reconstructed in Equation 6.

$$f(\theta,\phi) = \sum_{l=0}^{\infty} f_l(\theta,\phi) \quad \text{Equation 6}$$

Because space $V_l$ forms a rotation group, the norms of vectors in space $V_l$ will be rotation invariant. Thus, the identification and recognition process based on comparing the norms of the coefficients of the spherical harmonic expansion given by Equation 1 will be rotation invariant. The norm of the vector $f_l$ in space $V_l$ can be expressed as:

$$\|f_l\|^2 = \sum_{m=-l}^{l} |f_{lm}|^2 \quad \text{Equation 7}$$

In one example, there are N 3D object descriptors stored in the object database 36, denoted as $f^{(k)}(\theta,\phi), k=1, 2, \ldots, N$. The 3D object descriptors and spherical harmonic basis functions are accessed at 133 (FIG. 2) and compared to extracted information from the scan data at 135. the extracted information defines a detected object $f^{(T)}$. A match to the detected object $f^{(T)}$ can be found via rotation invariant spherical harmonics as shown in Equation 8.

$$\underset{k}{\operatorname{argmin}}\left(\sum_{l=0}^{L} W_l(\|f_l^{(T)}\|^2 - \|f_l^{(k)}\|^2)\right) \quad \text{Equation 8}$$

As shown in Equation 8, the match is defined to be the 3D object descriptor $f^{(k)}$ that minimizes the term inside the parenthesis. The number of frequency components L included for the match as well as the weights $W_l$ may be adjusted.

As discussed previously, the object database 36 may be constructed using one or more sources such as conventional 3-D laser profile scanners or CT scanners, one or more commercially available 3-D object databases, and may be updated to include new objects and profiles. Regardless of the source of the object data, the data may be converted to spherical harmonic representations, such as by using Equation 3.

The detected object $f^{(T)}$ (the object within the baggage to be tested and compared to the objects within the object database 36) can be constructed using contours and/or surfaces that enclose the object of interest. The contours and/or surfaces can be constructed using any known approaches such as marching cubes, gradient based, or other image processing methods. The detection of contours and surfaces allow the construction of the detected object $f^{(T)}$ based on Equation 3.

In some cases, the detected 3-D object $f^{(T)}$ may be constructed from partial information, such as one or more 2-D contours which may or may not be geometrically related. In such cases, the computation shown in Equation 3 may be integrated over well-defined regions.

Figure 3:
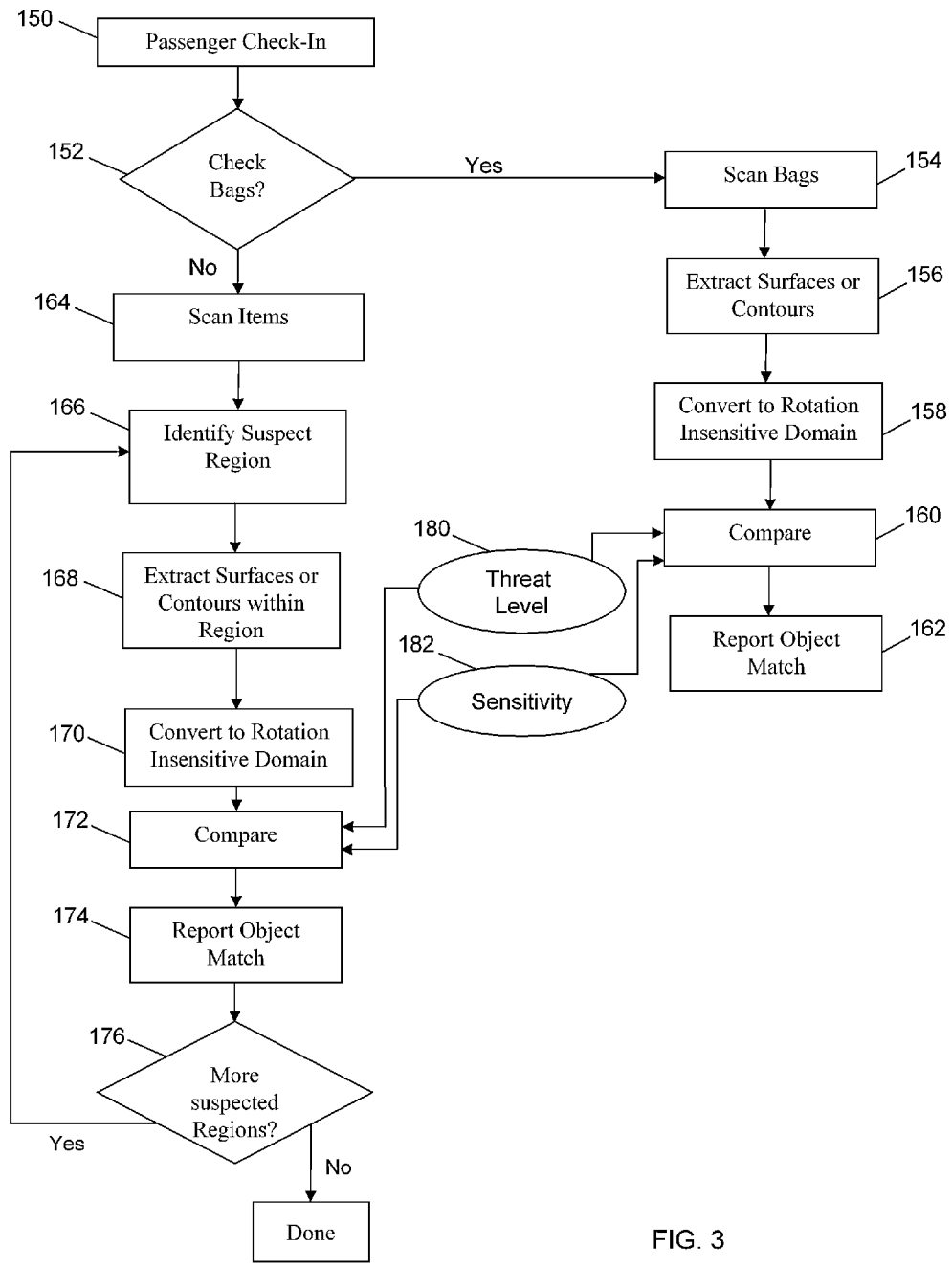
FIG. 3 illustrates using rotationally invariant data to compare the object data of objects detected within baggage to the object database in accordance with an embodiment of the invention.

FIG. 3 illustrates a method for electronically inspecting baggage, in accordance with one embodiment, using rotationally invariant data to compare the object data of objects detected within baggage to the object database 36. In this example, the object database 36 stores 3D object descriptors comprising spherical harmonic basis functions for the surfaces and the contours computed and stored therein. The comparing of the scan data to the object database 36 is shown to be different for checked baggage and carry-on baggage when boarding a plane or other mode of transportation, such as a ship, a train, a bus, and the like. Optionally, the same type of comparison may be performed for both checked and carry-on baggage. It should be understood that the same comparison and calculations may be used for any type of cargo to be transported/shipped to another location by air, freight, or ship, and the like.

When a passenger arrives with baggage at a point of departure (e.g., an airport terminal), at 150 the passenger checks-in with the carrier (e.g., airline, ship, or train), receives his/her ticket confirmation and proceeds to a security area for screening. If bags are checked at 152, the checked baggage is placed on a conveyor belt or otherwise removed from the immediate area and transferred to a secure area to be scanned. For checked baggage, the comparison may be accomplished automatically, without operator input.

At 154, the scanner 16 scans the checked-baggage as discussed, producing 2-D or 3-D data. For example, the scan data (e.g., the 3-D volumetric data set for each piece of baggage) generated by the scanner 16 is stored in the database 12. The scan data is downloaded from the scanner 16 to be stored in the database 12 in one of several image formats, for example, DICONDE, TIFF, JPEG, PDF, and the like. Each image file is assigned a header that identifies which scanner 16 produced the image, the time of the scan, the passenger ID, and other data obtained at the point of scan. The image files may be stored for forty-eight (48) hours or more. Optionally, the scanner 16 may produce rendered views that are pre-sorted and stored as a sequence of images in the database 12. The scan data may also be combined in data sets that are compressed and encrypted prior to storage in the database 12. Compressed and encrypted data sets may be conveyed over a high-speed connection such as network 24 with standard internet transport protocols to a requesting terminal/server or workstation 28.

At 156, the surfaces (for 3-D data) or contours (for 2-D data) are extracted. In some cases, items of similar density that are touching each other may be difficult to extract. Therefore, a partial surface or contour may be extracted.

At 158, the extracted surfaces and contours are each converted to a rotation insensitive domain, such as by accomplishing a spherical harmonic transform using Equation 3. In other words, the sum of squares or norm is determined and the surface or contour data is converted to spherical harmonic coefficients $f_{lm}$. Each surface and contour will have its own norm and/or spherical harmonic coefficients $f_{lm}$. In one embodiment, if the surfaces are determined to be of a single object, wherein the planes may or may not intersect each other, multiple norms may be combined into a single norm. The local workstation 14 or any other workstation 28 may access the data for review and/or processing.

At 160, the workstation 14 queries the object database 36 with the spherical harmonic coefficients $f_{lm}$ of the detected surface or contour. In other words, the database is searched to find objects that have the nearest norm to the query, such as by using Equation 8. The shapes within the object database 36 are represented by rotation invariant basis functions, such as spherical harmonic shape descriptors, and thus the identification of the 3-D shape may be performed quickly. For 2-D shapes, the 3-D spherical harmonic descriptor stored in the database is first converted to a 2-D contour by projecting the 3-D shape onto a number of different 2-D views. It should be understood that the projection may be pre-computed and stored in the object database 36 or may be performed in real-time upon receipt of the detected 2-D contour.

Potential object matches may be reported at 162. An object match may be an object in the object database 36 with the smallest norm. Alternatively, multiple objects having a norm within a certain tolerance or range may be returned for review. In one embodiment, all potential object matches may be reported, even if the object is considered to be benign. By identifying benign objects, it may be possible to electronically clear baggage that may have alarmed and would have had to be manually searched. Alternatively, only objects that are considered to be a threat may be reported.

If the detected object comparison process determines any organic material (e.g., typical bombs), illegal metal objects (e.g., guns, knifes, and the like) or detects any contraband, the passenger information database 20 may be accessed to determine the owner of the baggage. The luggage may be held and manually searched. In other cases, based on the level of detected threat, the owner of the baggage and all the baggage may be placed on a list for a manual inspection when the plane arrives.

Returning to 152, in addition to checked bags the passenger typically has items for carry-on that need to be scanned. When the passenger is in the security area, the passenger's carry-on baggage (e.g., purse, wallet, coat, jacket, shoes, back packs, baby strollers, briefcases, laptops, personal digital assistants, cell phones, and the like) that are being carried onto the plane (or a train, a bus, a ship and the like) are thus placed onto a conveyor belt within a container for scanning by the x-ray scanner 15 prior to passenger boarding.

At 164, the carry-on items are scanned by the scanner 15 or 16 to obtain a 2-D projection data set or volumetric 3-D data set (e.g., scan data) representative of the baggage. The scan data of the carry-on baggage may be stored in the database 12. The scanner 15 or 16 is connected to the local terminal/server or workstation 14 that has a display that shows projection or rendered images to a local screener to visually examine for any threats.

At 166, the screener may identify a suspected region of interest, such as by clicking on an area or by using a mouse, touchscreen or other interface to encircle or select a portion or subset of the data. For example, the screener may see a shape that may be a gun and wishes to have that area further examined. At 168 at least one contour or surface is extracted from within the indicated region. At 170 the contour or surface data is converted to the spherical harmonic domain to generate spherical harmonic coefficients, and at 172 the spherical harmonic data is compared to the object database 36. If one or more matches are found, at 174 the potential object match may be identified on the display of the workstation. Also, the operator may be notified if no match is identified. Optionally, the operator may be provided an indication of confidence wherein the match is rated by a percentage that may be associated with how close the norms were, or the match may be indicated as a very good, good or fair match. At 176, if the screener wishes to identify another region of interest the method returns to 166. Based on the match results, the carry-on items may be further searched, confiscated and/or returned to the passenger.

A threat level 180 and/or sensitivity 182 may be modified to adjust the number of possible object matches that are returned. For example, if the threat level at the airport or region is high, the threat level 180 or sensitivity 182 may be adjusted to return more possible object matches, such as by returning a greater range of norms. These additional matches may increase the number of bags that are manually screened and will increase the number of object images the screener may evaluate against the displayed actual object, which may be surface or volume rendered, for example. Increasing the threat level 180 and/or sensitivity 182 may also increase the number of false positives that are detected.

The method of FIG. 3 and the reported object match may further be used with other threat detection algorithms, such as explosives detection or weapons detection. For example, the reported object match may be presented to the threat detection system as an attribute to be used in combination with other information such as the CT number (Hounsfield unit) to determine the likelihood that the object may be an explosive.

Figure 4:
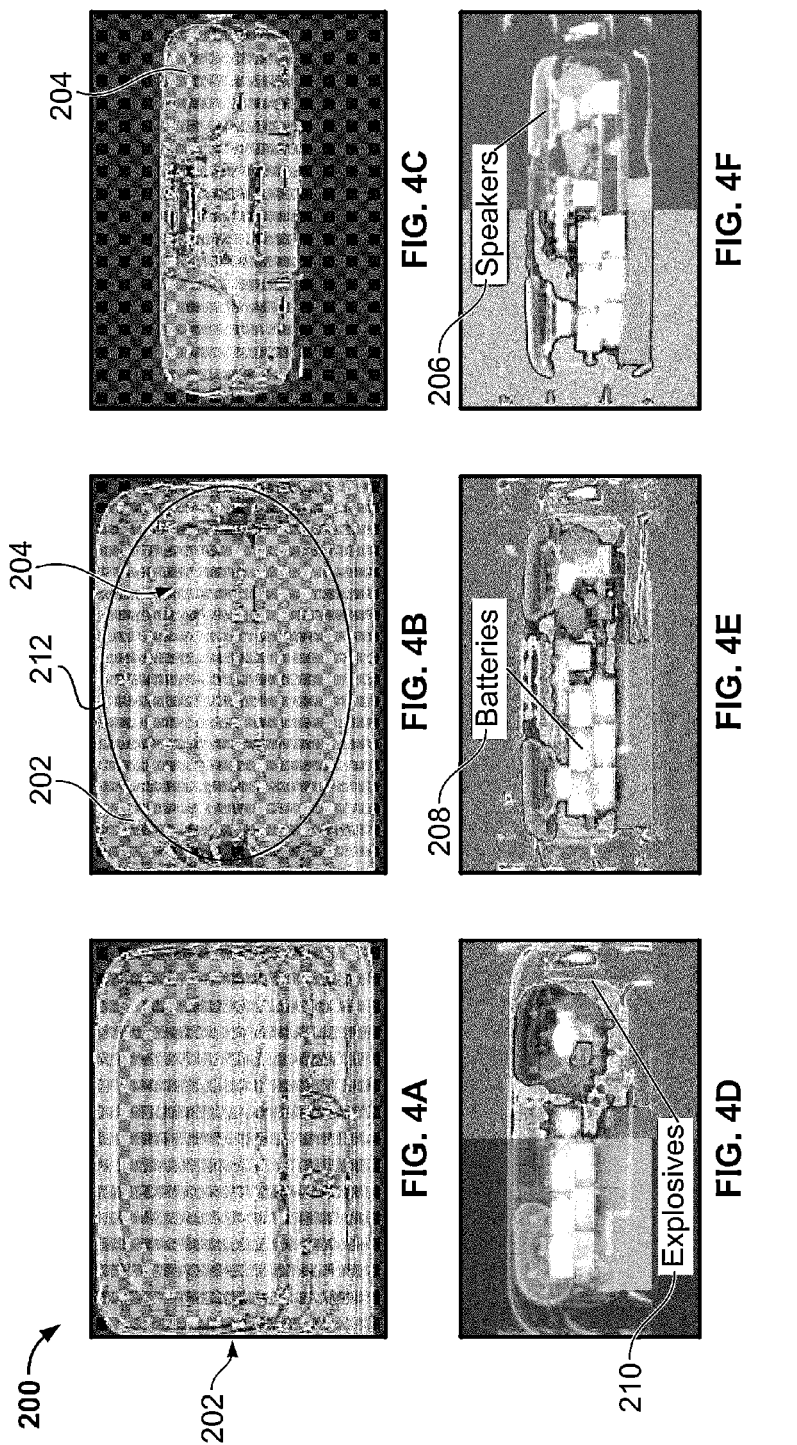
FIGS. 4A-4F illustrate views of exemplary structures within a piece of luggage formed in accordance with an embodiment of the invention.

FIG. 4 illustrates views of structures within a piece of luggage. The views may be displayed on the display of the workstation 14, or on any workstation 28 or remote viewing screens 30-34. FIG. 4(a) illustrates a surface rendering of the entire bag 202. Within the bag 202 an object 204 may be detected. The algorithm of FIG. 3 may detect the object 204 and perform the rendering and processing needed to extract the surface or contour (156 of FIG. 3). The surface rendering of the object 204 is shown in FIG. 4(c). The data is converted to rotation insensitive data (Equation 3) and compared to objects within the object database 36. This process is repeated for each detected structure within the bag 202, and further, within the object itself.

For example, the object 204 is a radio, and the object database 36 may return a result of "radio" to the operator. The result may be indicated in text, in a line or 3-D drawing or graphic that most closely represents the best match, and may also indicate a confidence level, such as 90 or 95 percent confidence that the object is a radio. The radio may be classified as benign, but the benign classification may not extend to any structure detected within the radio.

In one example, to view a structure within the object 204, the CT raw scan data is volume rendered with color transparencies as shown in FIGS. 4(d), 4(e), and 4(f). Different objects may be indicated differently or groups of objects may be indicated similarly, such as with the same color or shading. Two objects 206 are indicated and the object database 36 may return a result of speakers. A group of objects 208 may return a result of batteries, and two objects 210 may return a result of explosive stimulants (e.g., as soap bars) that are hidden underneath the right speaker. Although the speakers and batteries may be expected, the speakers may be indicated as benign while the batteries may be indicated as a potential threat. The two objects 210 may be indicated as a high threat.

In another embodiment, the local scanner may select an object within the bag 202 for investigation. The scanner may use the user interface to click on or otherwise indicate a region of interest (ROI) 212, such as by encircling the object 204 (166 of FIG. 3). The workstation 14 then evaluates the data within the ROI 212 and attempts to match any structures found via comparison with the object database 36.

Figure 5:
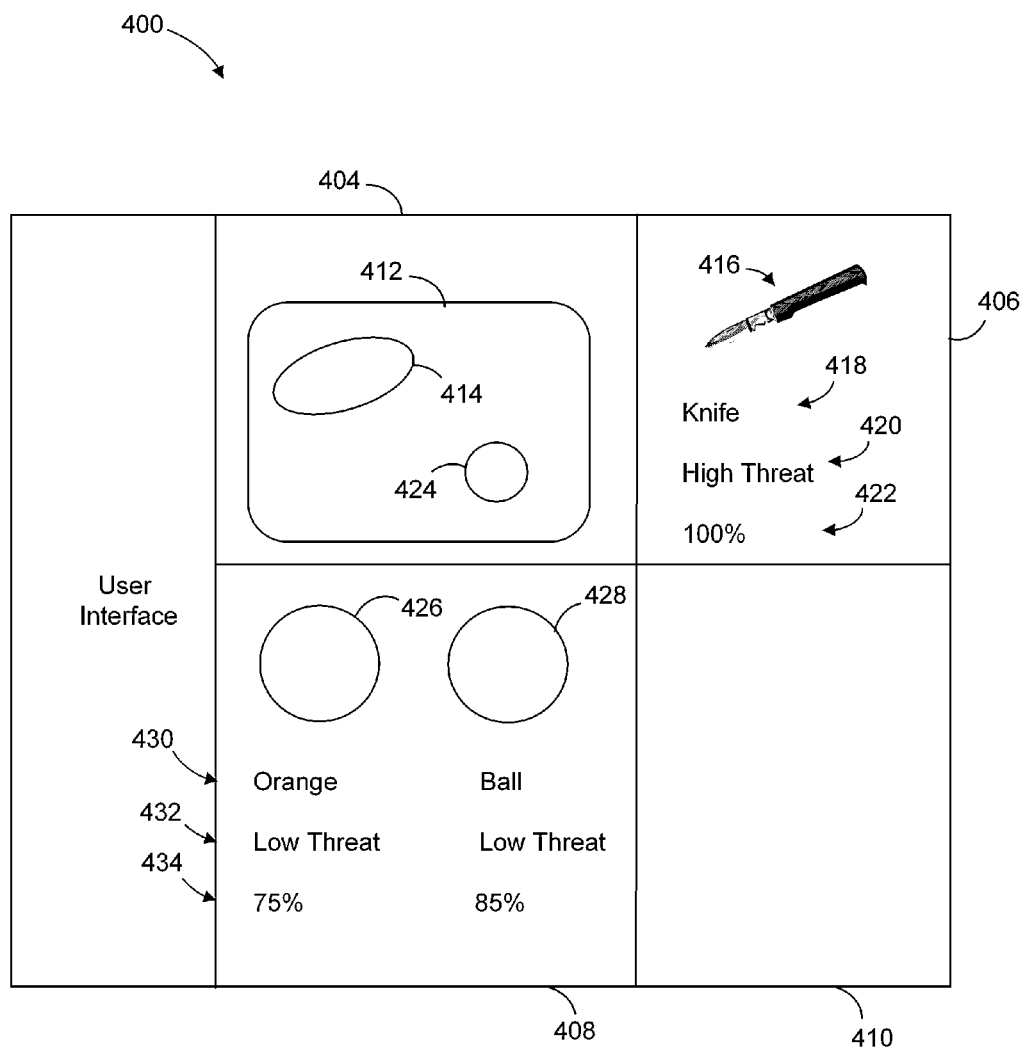
FIG. 5 illustrates an embodiment of a display at a local screener's terminal formed in accordance with an embodiment of the present invention.

FIG. 5 illustrates an embodiment of a display 400 as shown on a local screener's workstation 14. The display 400 provides a user interface 402 and multiple display windows 404, 406, 408 and 410. It should be understood that more or less windows 404-410 may be used, and that the size of the windows may change based on the application and/or input by the screener. The screener may select to display a current scanned image 412 in a first display window 404. The current scanned image 412 may be a 3-D image, a 2-D image, volume rendering, surface rendering, or other selected display. The screener may use the user interface 402 to select an ROI 414 within the scanned image 412.

The workstation 14 may then extract the surface or contour of objects within the ROI 414. In one embodiment, the surface or contour data is converted to the rotation insensitive domain, such as by converting to spherical harmonic coefficients. The workstation 14 then compares the rotation insensitive data within the ROI 414 to rotation insensitive data within the object database 36. In another embodiment, the workstation 14 may compare the extracted surface or contour to surfaces or contours, respectively, within the object database 36.

Any matched object and/or description of matching objects may be displayed in the window 406. An image 416 of the matched object from the object database 36 may be displayed, in this example, an image of a knife. The object database 36 may instead or additionally provide a description 418, a threat indicator 420, and/or an indication of confidence 422 that may indicate how close a match the object within the ROI 414 and the item returned from the object database 36 are.

The security official 26 may select additional areas of interest, such as ROI 424. After querying the object database 36, any matched images may be displayed, such as in window 408. In this example, the object database 36 may return more than one item, such as images 426 and 428. Associated descriptions 430, threat indicators 432, and indications of confidence 434 may also be displayed.

The security official 26 may choose to display other matched items or other types of views in window 410. Based on the results from the object database comparison as well as other threat detection algorithms that may be running concurrently, the screener may indicate that the bag should be manually searches or the bag may be cleared.

In the above examples, the screener 16 are described in connection with CT and x-ray line scanners and the raw data sets are described in connection with attenuation measurement data. For instance the scanners 16 may include a cine computed tomography scanner, a helical CT scanner, a dual-energy x-ray scanner, dual-energy CT scanner, and a four-dimensional (4-D) cine computed tomography scan. However, alternatively other types of scanners 16 and other types of raw data may be obtained, processed and displayed without departing from the meets and bounds of the present invention. For example, the scanner 16 may represent an electron beam scanner. Alternatively, the scanner 16 may transmit and receive non-x-ray forms of energy, such as electromagnetic waves, microwaves ultraviolet waves, ultrasound waves, radio frequency waves and the like. Similarly, in the above described embodiments, the raw data set may be representative of attenuation measurements taken at various detector positions and projection angles, while the object is stationary within the scanner 16 or while the object is continuously moving through the scanner 16 (e.g., helical or spiral scanning). Alternatively, when non-x-ray forms of energy are used, the raw data set may represent non-attenuation characteristics of the object. For example, the raw data may represent an energy response or signature associated with the object and/or the content of the object, wherein different types of objects may exhibit unique energy responses or signatures. For example, explosives, biological agents, and other potentially threatening medium, may exhibit unique electromagnetic responses when exposed to certain fields, waves, pulse sequences and the like. The electromagnetic response of the object and the content of the object are recorded by the scanner 16 as raw scan data stored in the database 12. As a further example, the scanner 16 may be used to obtain finger prints from the object. The finger prints would be recorded as scan data in the database 12.

Figure 6:
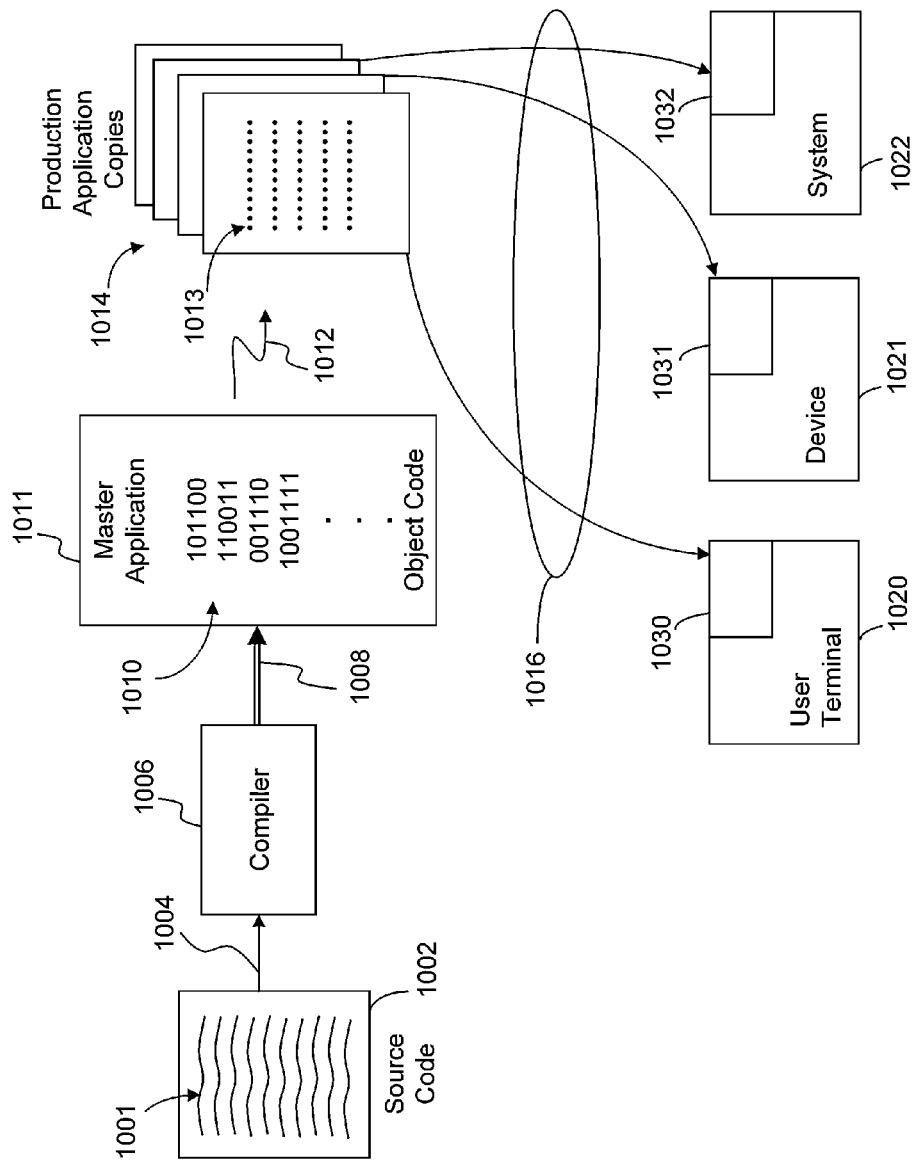
FIG. 6 illustrates a block diagram of exemplary manners in which embodiments of the present invention may be stored, distributed and installed on computer readable medium.

FIG. 6 illustrates a block diagram of exemplary manners in which embodiments of the present invention may be stored, distributed and installed on computer readable medium. In FIG. 6, the "application" represents one or more of the methods and process operations discussed above. For example, the application may represent the process carried out in connection with FIGS. 2-3 and 5 as discussed above.

As shown in FIG. 6, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous types, as denoted by path 1012, to produce production application copies 1013 that are saved on separate production computer readable medium 1014. The production computer readable medium 1014 are then conveyed, as denoted by path 1016, to various systems, devices, terminals and the like. In the example of FIG. 6, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, intercontinental and the like.

The operations noted in FIG. 6 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but product production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A method of electronically inspecting baggage, comprising:
    generating scan data representative of a piece of baggage;
    extracting at least one of contour and surface information from the scan data, the at least one of contour and surface information representative of an object within the baggage;
    converting the at least one of contour and surface information to spherical harmonic coefficients;
    performing a weighted comparison of the spherical harmonic coefficients to an object database to identify an object match, the object database comprising spherical harmonic coefficients representative of shapes of known objects; and
    presenting the object match.

2. The method of claim 1, wherein the scan data is generated by a scanner having at least one source and producing at least two views, the at least two views being used to extract the at least one of contour and surface information.

3. The method of claim 1, wherein the scan data is 2-D slices and the extracting further comprises extracting the at least one of contour and surface information surfaces based on a subset of the 2-D slices.

4. The method of claim 1, wherein the scan data is generated by a CT scanner having a moving source and detector, the CT scanner producing a volume from which the at least one of contour and surface information is extracted.

5. The method of claim 1, wherein the scan data is generated by an x-ray scanner having a stationary source and detector, the x-ray scanner producing at least one view from which the at least one of contour and surface information is extracted.

6. The method of claim 1, further comprising:
    identifying at least one of a threat level and a sensitivity; and
    adjusting the at least one of a threat level and sensitivity to increase or decrease an amount of the object matches.

7. The method of claim 1, further comprising identifying a region of interest with a user interface, the region of interest comprising a subset of the scan data, the extracting being based on the region of interest.

8. The method of claim 1, where extracting at least one of contour and surface information is performed with a partially available or truncated data that only represents a portion of the object.

9. The method of claim 1, further comprising electronically unpacking the baggage to identify the object within the baggage.

10. The method of claim 1, further comprising:
    electronically unpacking the baggage to identify the object within the baggage; and
    determine a volume for each object within the baggage.

11. The method of claim 1, further comprising:
    electronically unpacking the baggage to identify the object within the baggage, wherein electronically unpacking the baggage includes:
    displaying a three-dimensional (3D) rendering of the contents within the baggage;
    permitting a user to select the object in the baggage contents;

removing the object selected by the user; and displaying the remaining contents within the baggage to enable the user to visually observe a 3D rendering of the contents remaining within the baggage.

12. The method of claim 1, wherein performing a weighted comparison further comprises applying a first weight to a first weighted comparison having a first frequency value and applying a second weight to a second weighted comparison, the first weight being different than the second weight.

13. The method of claim 1, wherein performing a weighted comparison further comprises applying a first weight to a first weighted comparison having a first frequency value and applying a second weight to a second weighted comparison, the first frequency value being larger than the second frequency value and the first weight being larger than the second weight.

14. A system for electronically inspecting baggage, comprising:

a database to store scan data acquired while scanning a piece of baggage;

an object database to store spherical harmonic coefficients corresponding to known objects;

a workstation for generating a plurality of spherical harmonic coefficients of an object of interest in the piece of baggage and performing a weighted comparison of the spherical harmonic coefficients of the object of interest in the baggage to the spherical harmonic coefficients corresponding to the known objects to identify an object match; and a display for displaying information related to the object match.

15. The system according to claim 14, further comprising a scanner configured to scan the baggage, the scanner comprising at least one of a computed tomography (CT) scanner, a cine computed tomography scanner, a helical CT scanner, a four-dimensional (4D) cine computed tomography scanner, an electronic beam scanner, a DI scanner, an X-ray scanner, a dual-energy x-ray scanner, and a dual-energy CT scanner.

16. The system according to claim 14, further comprising an operator input for identifying a portion of the scan data to be compared to the shape information within the object database.

17. The system according to claim 14, wherein the workstation segments the scan data to identify 3-D objects, the workstation extracting at least one of surface and contour information based on the 3-D objects, the workstation converting the surface and contour information to the spherical harmonic coefficients.

18. The system according to claim 14, wherein the at least one of contour and surface information related to the object match comprises at least one of an image, a description, a threat indicator, and an indication of confidence associated with the object match.

19. The system according to claim 14, wherein the object database comprises at least one of a commercially available database and images generated using a scanner, the object database being updateable by one of removing objects and adding additional objects.

20. A non-transitory computer readable medium storing an application for use to inspect baggage, where scan data has been generated that is representative of a piece of baggage, the scan data being stored at a first memory, the application comprising instructions configured to direct a computer to:

obtain the scan data from the first memory;

extract at least one of contour and surface information from the scan data, the at least one of contour and surface information representative of an object within the baggage;

convert the at least one of contour and surface information to spherical harmonic coefficients;

perform a weighted comparison of the spherical harmonic coefficients to an object database to identify an object match, the object database including spherical harmonic coefficients of known objects; and present the object match on a display.

21. The non-transitory computer readable medium of claim 20, wherein the object database comprises shape information representative of shapes of known objects, the shape information being stored based on spherical harmonic coefficients.

22. The non-transitory computer readable medium of claim 21, wherein the instructions are further configured to receive an input from a user identifying a region of interest within the scan data, the extracting operating on the scan data within the region of interest.

* * * * *